US007229551B2

(12) United States Patent
Murata et al.

(10) Patent No.: US 7,229,551 B2
(45) Date of Patent: Jun. 12, 2007

(54) DIFFUSION PROMOTING DEVICE FOR LOW FLOW VELOCITY GRADIENT HIGH PERFORMANCE LIQUID CHROMATOGRAPHY

(75) Inventors: Kaoru Murata, Ibaraki (JP); Nariyasu Mano, Ibaraki (JP); Naoki Asakawa, Ibaraki (JP)

(73) Assignee: Eisai Co., Ltd., Tokyo (JP)

( * ) Notice: Subject to any disclaimer, the term of this patent is extended or adjusted under 35 U.S.C. 154(b) by 23 days.

(21) Appl. No.: 10/876,472

(22) Filed: Jun. 28, 2004

(65) Prior Publication Data

US 2005/0000875 A1    Jan. 6, 2005

Related U.S. Application Data

(62) Division of application No. 09/831,496, filed as application No. PCT/JP99/06336 on Nov. 12, 1999, now Pat. No. 6,780,325.

(30) Foreign Application Priority Data

Nov. 18, 1998    (JP) .................... 10-328465

(51) Int. Cl.
*B01D 15/08* (2006.01)
(52) U.S. Cl. .................... 210/198.2; 210/656; 210/659
(58) Field of Classification Search ................ 210/635, 210/656, 659, 198.2
See application file for complete search history.

(56) References Cited

U.S. PATENT DOCUMENTS 4,475,821 A    10/1984  Koch et al.
4,942,018 A    7/1990   Munk
5,117,109 A    5/1992   Asakawa et al.
6,780,325 B1 *  8/2004   Murata et al. .............. 210/656

FOREIGN PATENT DOCUMENTS

| DE | 91 07 564 U1 | 9/1991 |
|---|---|---|
| EP | 0 263 567 | 4/1988 |
| EP | 0 377 202 A2 | 7/1990 |
| JP | 59-94064 | 5/1984 |
| JP | 60183554 | 9/1985 |
| JP | 62-241532 | 10/1987 |
| JP | 2-32931 | 3/1990 |
| JP | 3-277966 | 12/1991 |
| WO | WO 96/26000 A1 | 8/1996 |

OTHER PUBLICATIONS

Snyder, Introduction to Modern Liquid Chromatography, 1979, John Wiley and Sons, Inc., pp. 560-561.
Abstract of Japan Patent No. 3-175355 published Jul. 30, 1991.
Abstract of WO 97/03070 Jan. 30, 1997.

* cited by examiner

*Primary Examiner*—Ernest G. Therkorn
(74) *Attorney, Agent, or Firm*—Birch, Stewart, Kolasch & Birch, LLP (57) ABSTRACT

Device for improving detection sensitivity in low flow velocity high performance liquid chromatographic apparatus. Preferredly, diffusion promoting device connected at just before separation column and having function of improving detection sensitivity for use in low flow velocity high performance liquid chromatographic apparatus. Also, method for improving detection sensitivity in low flow velocity high performance liquid chromatographic apparatus.

6 Claims, 7 Drawing Sheets

DIFFUSION PROMOTING DEVICE FOR LOW FLOW VELOCITY GRADIENT HIGH PERFORMANCE LIQUID CHROMATOGRAPHY

This application is a divisional of U.S. application Ser. No. 09/831,496, filed on May 10, 2001, the entire contents of which are incorporated by reference herewith, now U.S. Pat. No. 6,780,325, which, in turn, is a 371 of PCT/JP99/06336 filed Nov. 12, 1999.

TECHNICAL FIELD

The present invention relates to a diffusion promoting device connected to just before a separation column and having a function for improving detection sensitivity in a low flow velocity gradient high performance liquid chromatography system, to a method for improving detection sensitivity of a target component by connecting the diffusion promoting device, and to an analytical method using the system.

PRIOR ART

High performance liquid chromatography has been frequently used for analyzing a trace amount of components in a sample. In recent years, high performance liquid chromatography is used in a system for simultaneously separating and identifying the component in a high sensitivity by combining with a mass spectrometer or a nuclear magnetic resonance spectrometer. For example, JP-A 3-175355 discloses an apparatus and a method for conversion of mobile phases in a high performance liquid chromatography-mass spectrometer system, and an apparatus for trapping a target components in a trapping column.

However, the permissible flow velocity of the mobile phase capable of flowing into the mass spectrometer is several tens microliters/min in the high performance liquid chromatography-mass spectrometer system from the view point of analytical accuracy of the mass spectrometer. A tube having a smaller inner diameter than conventional tubes is often used in the low flow velocity high performance liquid chromatography system as described above, in order to suppress diffusion of the target component in the tube of a liquid flow line. The inner diameter of the tube is generally determined by considering the inner diameter of a separation column and linear velocity in the tube.

When a tube having an inner diameter of 0.1 mm or less is used in the low flow velocity high performance liquid chromatography system, however, the tube may be blocked with fine particles to make an analysis by low flow velocity high performance liquid chromatography difficult.

It is known in the art, on the other hand, that an effect for concentrating the target component at the top portion of the separation column may be obtained when a gradient elution method is used in low flow velocity high performance liquid chromatography, that is in low flow velocity gradient high performance liquid chromatography. For example, JP-A 3-175355 discloses an example in which a tube having a larger inner diameter than usual, i.e. 0.8 mm, and a length of 100 mm is connected at just before the separation column for efficiently obtaining the concentration effect. It reports that a gradient effect is obtained in the tube and peak resolution is improved by using such column as described above. However, since a tube as long as 100 mm is used in the method described above, it may be conjectured that improvement of resolution is not always realized depending on the kind of the separation column used, and on analysis conditions in high performance liquid chromatography.

Accordingly, development of an apparatus capable of enhancing analytical and quantitative sensitivity is urgently desired-in the low flow velocity gradient high performance liquid chromatographic apparatus for analysis and assessment of a trace amount of biological components, and impurities in environmental samples and pharmaceuticals.

DISCLOSURE OF INVENTION

The inventors of the present invention has found, through intensive studies considering the situations as described above, that the desired objects can be attained by the construction as described below.

The present invention provides a diffusion promoting device provided just before a separation column and having a function for improving detection sensitivity, in a low flow velocity high performance liquid chromatographic apparatus.

The present invention also provides a method for improving detection sensitivity of a target component for use in a low flow velocity gradient high performance liquid chromatographic apparatus, wherein a diffusion promoting device is provide just before a separation column.

The present invention further provides a method for analyzing a trace amount of the target component for use in a low flow velocity high performance liquid chromatographic apparatus by concentration, diffusion and separation of the target component to be analyzed in the sample.

The diffusion promoting device comprises a solvent inlet tube and outlet tube, which satisfies 1) a part of either the solvent inlet tube or the solvent outlet tube has a larger inner diameter than the other does or 2) the solvent inlet tube and outlet tube are connected with a given angle with each other, or both 1) and 2).

The diffusion promoting device is connected between a component concentration column and the separation column through a tube in the low flow rate gradient high performance liquid chromatography system in which the component concentration column is connected at just before the separation column. The diffusion promoting device has a function by which a sample band containing the target component eluted from the component concentration column is diffused by changing the solvent flow passageway in the device to form a homogeneous solution. Since this homogeneous solution is introduced into the separation column, a concentrating effect of the component at the top portion of the separation column in gradient elution is efficiently exerted. Consequently, theoretical plates of the separation column to be used for assessment of the target component is increased while improving the peak shape of the component, thereby enabling sensitivity of qualitative detection of the target component to be improved.

A tubing with an inner diameter of 0.1 m or less is usually used in low flow velocity gradient high performance liquid chromatography system. However, it is possible to improve detection sensitivity of the target component in the low flow velocity gradient high performance liquid chromatography system in which the diffusion promoting device according to the present invention is connected, by, for example, making the inner diameter of a part of the solvent inlet tube and outlet tube in the device to be larger (an inner diameter of 0.13 mm or 0.25 mm) than the other part, and by using a tube with an inner diameter of 0.13 mm or less for the other portion of the line. It is also possible to prevent the inside of the tube connected at just before the separation column and the inside of the separation column from being clogged, by elongating the portion having a large inner diameter between the solvent inlet and outlet tubes in the diffusion promoting device.

The given angle formed between the solvent inlet tube and outlet tube in the diffusion promoting device may be any one of an acute angle, a rectangle and an obtuse angle. Otherwise, a frit membrane may be inserted into the diffusion promoting device. While examples of the frit (membrane) include a sintered filter, a ceramic, a metal mesh or a cellulose membrane, they are not necessarily restricted thereto.

In particular, the diffusion promoting device comprises a solvent inlet tube and outlet tube, which satisfies 1) a part of either the solvent inlet tube or the solvent outlet tube has a larger inner diameter than the other portion or 2) the solvent inlet tube and outlet tube are connected with a given angle with each other, or both 1) and 2), and wherein a frit (membrane) is inserted in the inlet tube and/or outlet tube, both objects of promoting diffusion of the target component and efficiently preventing clogging of the separation column with fine particles in the separation column can be simultaneously attained.

The diffusion promoting device may display the functions for improving detection sensitivity and/or for preventing clogging in the device, so long as the device is assembled into low flow velocity high performance liquid chromatographic apparatus. The low flow velocity high performance liquid chromatographic apparatus includes, for example, a gradient micro high performance chromatographic apparatus having a micro column with an inner diameter of 0.5 to 1 mm and being used at a flow velocity of several tens microliters per minutes, a gradient semi-micro high performance liquid chromatographic apparatus having a semi-micro column with an inner diameter of 1 to 2.5 mm and being used at a flow velocity of 50 to 250 µl/min, or a gradient capillary high performance liquid chromatographic apparatus having a capillary column with an inner diameter of 0.5 mm or less and being used at a flow velocity of several microliters per minutes.

The diffusion promoting device is preferably provided at just before the separation column, more preferably between the component concentration column and separation column, in the low flow velocity liquid chromatographic apparatus.

While one example of the low flow velocity liquid chromatographic apparatus in which the diffusion promoting device according to the present invention is connected at just before the separation column is described in detail hereinafter, the present invention is by no means restricted thereto.

Figure 8:
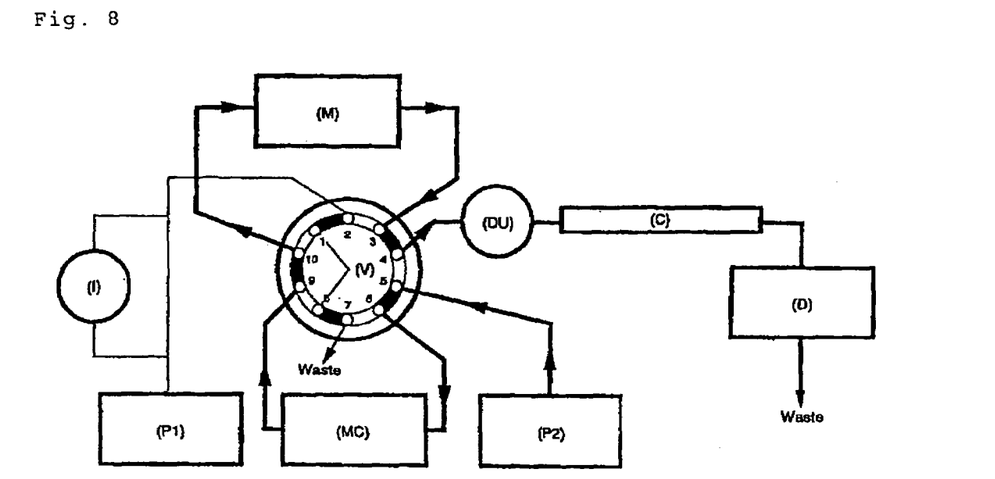
FIG. 8 illustrates a low flow velocity gradient high performance chromatographic apparatus in which a diffusion promoting device is connected at just before a separation column.

As shown in FIG. 8, the present invention provides a low flow velocity high performance liquid chromatographic apparatus in which a solvent pump (P1), an injector (I), a switching valve (V), a component concentration column (M), a switching valve (V), a solvent mixer (MC) and a switching valve (V) are connected in this order in one line, and a solvent pump (P2), a switching valve (V), a diffusion promoting device (DU), a separation column (C) and a detector (D) are connected in another-line.

The present invention also provides a method for analyzing a trace amount of a component in a sample with high detection sensitivity for use in the low flow velocity gradient high performance liquid chromatographic apparatus, wherein the target component is trapped in the component concentration column (M) by means of a mobile phase discharged from the solvent pump (P1), the switching valve (V) is turned to discharge another mobile phase using a solvent pump (P2), and the target component is eluted from the separation column (C) through diffusion of the target component using the diffusion promoting device (DU).

Figure 9:
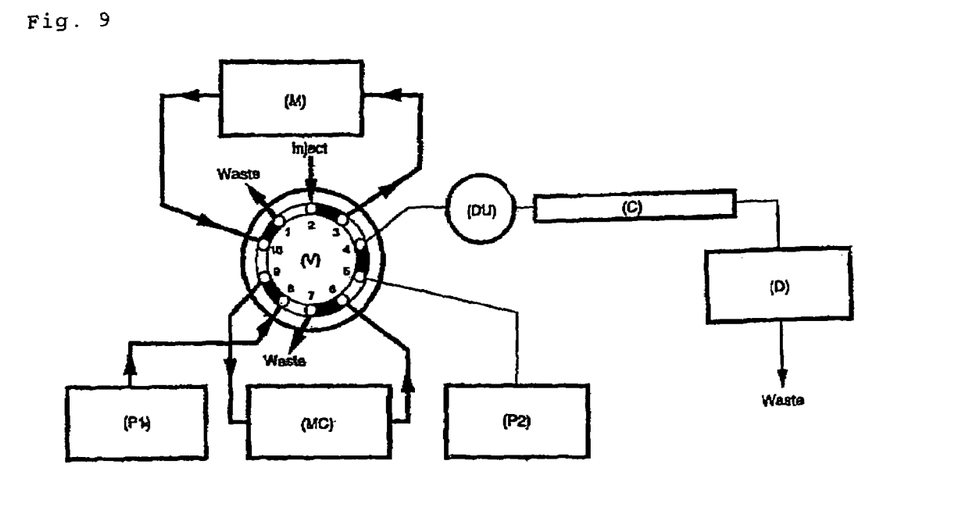
FIG. 9 illustrates a low flow velocity gradient high performance chromatographic apparatus in which a diffusion promoting device is connected at just before a separation column.

As shown in FIG. 9, the present invention provides a low flow velocity high performance liquid chromatographic apparatus in which a solvent pump (P1), a switching valve (V), a solvent mixer (MC) and a switching valve (V) are connected in this order in one line, and a solvent pump (P2), a switching valve (V), a diffusion promoting device (DU), a separation column (C) and a detector (D) are connected in another line, and a switching valve (V), a component concentration column (M) and a switching valve (V) are connected in a different line. The present invention also provides a method for analyzing a trace amount of a component in a sample with high detection sensitivity for use in the low flow velocity gradient high performance liquid chromatographic apparatus, wherein the target component is injected into the component concentration column (M) while filling a solvent in the solvent mixer (MC) by means of the solvent pump (P1), the switching valve is turned to discharge a mobile phase by means of a solvent pump (P2), and the target component is eluted from the separation column (C) through diffusion of the target component using the diffusion promoting device (DU).

Although the diffusion promoting device according to the present invention manufactured by machining and combining the solvent inlet tube and solvent outlet tube may be used as an exposed device, it may be housed in a small size vessel. The materials for the solvent inlet and outlet tubes, and for the vessel are not particularly restricted.

While the small size vessel easy for use may be a linear union, a triangular union or a T-shaped union, the solvent inlet tube and outlet tube are desirably tightly screwed using, for example, ferrules in order to prevent the mobile phase from leaking.

While examples of the diffusion promoting device are illustrated in FIGS. 1 to 7, the device is by no means restricted thereto.

While the solvent inlet tube (1) is connected to the component concentration column, and the solvent outlet tube (2) is connected to the separation column in the diffusion promoting devices shown in FIGS. 1 to 7, they may be connected in a reverse order with each other. For example, a good diffusion promoting effect may be obtained when the tube (1) is connected to the separation column and the tube (2) is connected to the component concentration column.

Figure 1:
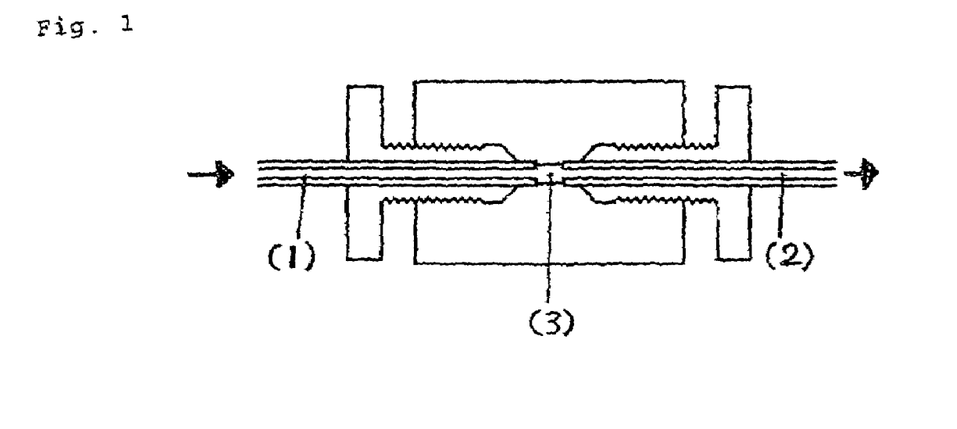
FIG. 1 illustrates a diffusion promoting device comprising a solvent inlet tube (1) and outlet tube (2), a part (3) of the solvent inlet tube or outlet tube having a larger inner diameter than the other portion of the tube.
Figure 2:
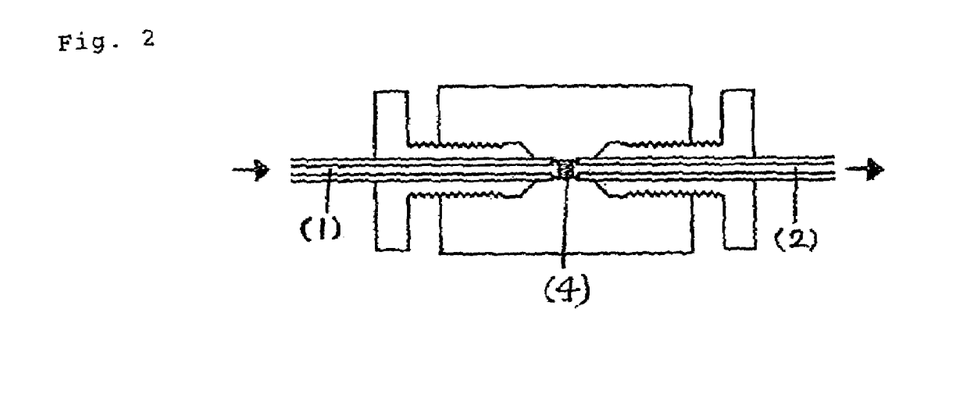
FIG. 2 illustrates a diffusion promoting device comprising a solvent inlet tube (1) and outlet tube (2), a part (3) of the solvent inlet tube or outlet tube having a larger inner diameter than the other portion of the tube, and a frit (4) being inserted into the portion having a larger inner diameter.

FIG. 1 shows an example using the liner union in which the inner diameter of a part (3) of the solvent inlet tube (1) and outlet tube (2) is larger than the other portion, and FIG. 2 shows an example in which a frit (4) is inserted into the part (3) having a larger inner diameter than the other portion in the diffusion promoting device.

Figure 3:
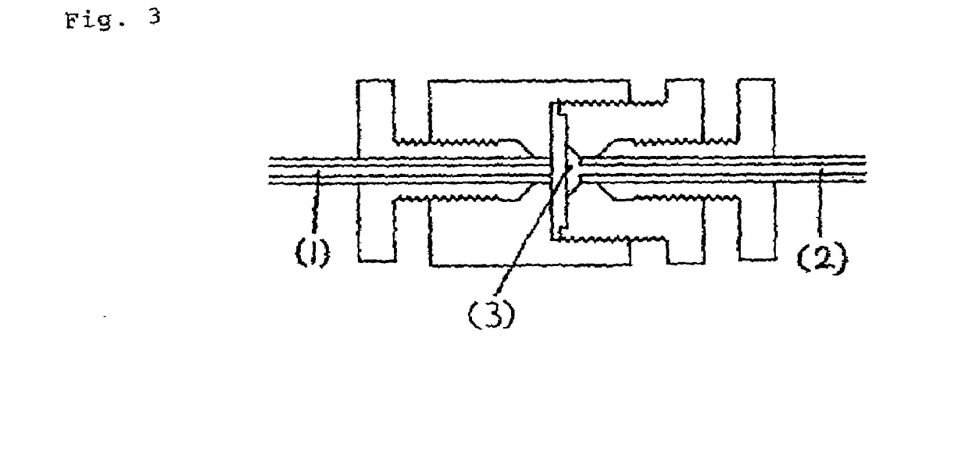
FIG. 3 illustrates a diffusion promoting device comprising a solvent inlet tube (1) and outlet tube (2), a part (3) of the solvent inlet tube or outlet tube having a larger inner diameter than the other portion of the tube, and the portion having a larger inner diameter being tapered.
Figure 4:
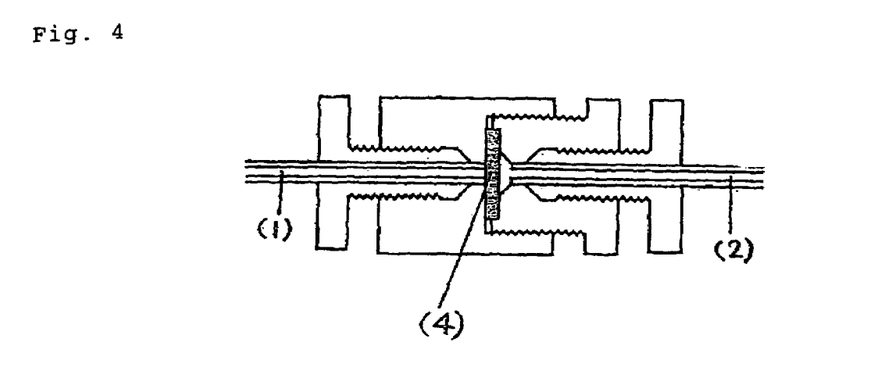
FIG. 4 illustrates a diffusion promoting device comprising a solvent inlet tube (1) and outlet tube (2), a part (3) of the solvent inlet tube or outlet tube having a larger inner diameter than the other portion of the tube, the portion having a larger diameter being tapered, and a flit (4) being inserted in front of the tapered portion.

FIG. 3 shows the diffusion promoting device with the same mechanism as that in FIG. 1, wherein a part (3) of the solvent inlet tube (1) and outlet tube (2) also has a lager inner diameter than the other portions. FIG. 4 shows the diffusion promoting device in which the flit (4) is inserted into the portion (3) having a larger inner diameter than the other portion in the device. In a preferred example as shown in FIGS. 3 and 4, the passageway of the mobile phase in the diffusion promoting device is tapered from the inlet tube (1) toward the outlet tube (2), or from the outlet tube (2) toward the inlet tube (1), in order to facilitate diffusion of the sample in the diffusion device.

Figure 5:
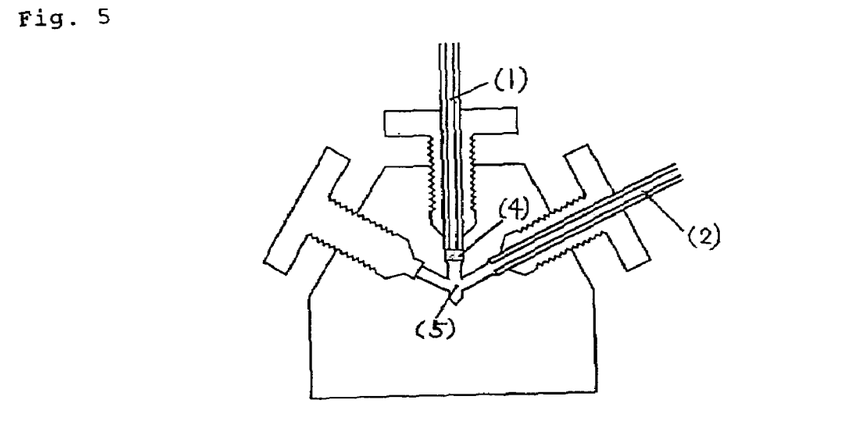
FIG. 5 illustrates a diffusion promoting device in which the solvent inlet tube (1) and outlet tube (2) are connected forming an acute angle.
Figure 6:
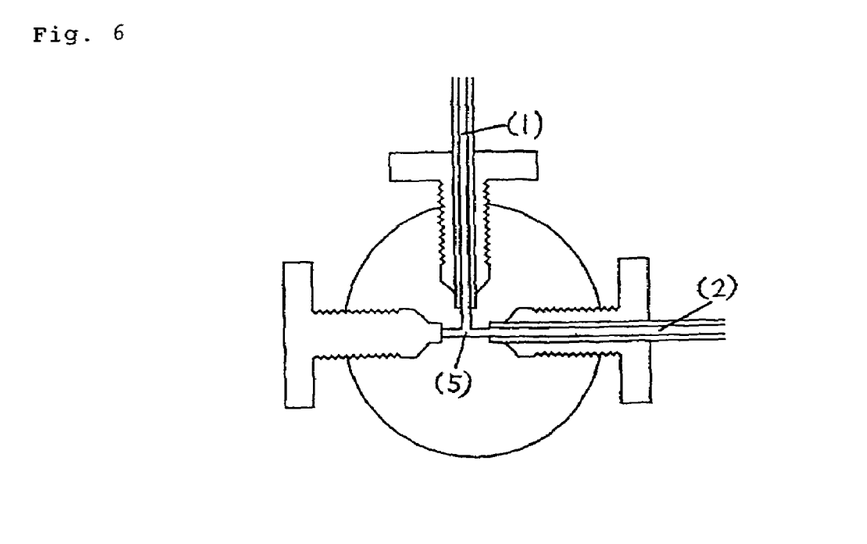
FIG. 6 illustrates a diffusion promoting device in which the solvent inlet tube (1) and outlet tube (2) are connected forming a rectangle.
Figure 7:
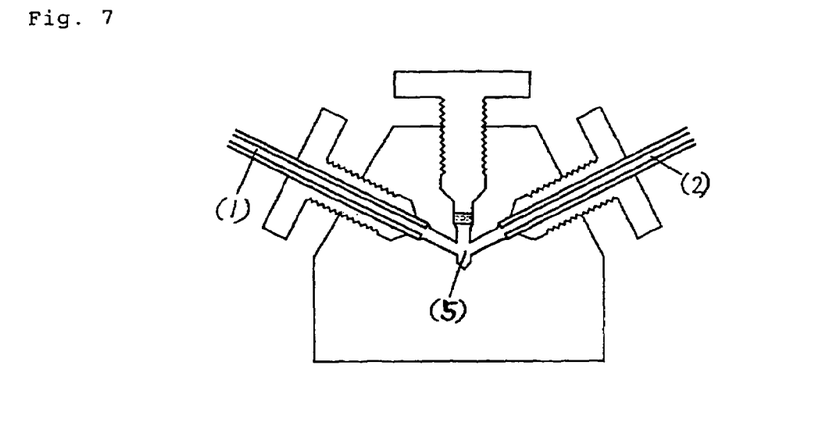
FIG. 7 illustrates a diffusion promoting device in which the solvent inlet tube (1) and outlet tube (2) are connected forming an obtuse angle.

In the diffusion promoting device shown in FIGS. 5 to 7, the solvent inlet tube (1) is connected to the solvent outlet tube (2) with a given angle. For example, the triangular union is used in the device shown in FIGS. 5 and 7, and the T-shaped union is used in the device shown in FIG. 6. The angles formed between the inlet tube (1) and outlet tube (2) is an acute angle, a rectangle and an obtuse angle in the devices shown in FIGS. 5, 6 and 7, respectively. These angles between the tubes functions to change the solvent passageway to thereby allow the sample band to diffuse. As shown in FIG. 5, a frit (4) such as a line filter may be inserted into a part of the tube in the device.

A system being improved in detection sensitivity and suitable for high speed, high sensitivity analysis of trace components may be constructed by integrating the diffusion promoting device into the low flow velocity gradient high performance liquid chromatography system configured as described below.

The system according to the present invention will be described in detail with reference to FIG. 8.

FIG. 8 illustrate the low flow velocity gradient high performance liquid chromatography system in which a solvent pump (P1), an injector (I), a switching valve (V), a component concentration column (M) comprising a diffusion membrane and an absorption membrane, a switching valve (V), a solvent mixer (MC) and a switching valve (V) are connected in this order in one line, and a solvent pump (P2), a switching valve (V), the diffusion promoting device (DU), a separation column (C) and a detector (D) are connected in another line. The concentration and separation method in this low flow velocity gradient high performance liquid chromatography method is as follows.

(A) A mobile phase for component concentration is discharged from the solvent pump (P1), the sample solution is injected into the injector (I), and the sample is injected into the component concentration column (M) while diluting the sample solution with a mobile phase for component concentration to trap the target component in the sample into the component concentration column (M). The solvent mixer is simultaneously filled with the mobile phase for component concentration. The mobile phase for component concentration serves as a mobile phase for allowing the target component to be absorbed in the component concentration column, which is a solvent having a relatively large polarity such as water when the component concentration column is hydrophobic.

(B) Then, the mobile phase for sample separation discharged from the pump (P2) is eluted by turning the valve (V) through the solvent mixer (MC), sample concentration column (M), diffusion promoting device (DU), separation column (C) and detector (D). The mobile phase for sample separation serves as a mobile phase for eluting the sample components from the sample component concentration column (M) and separating the sample components through separation column (C). A solvent having smaller polarity than the mobile phase such as methanol and acetonitrile is used for component concentration when the component concentration column (M) is hydrophobic. The mobile phase for component concentration is mixed with the mobile phase for sample separation by means of the solvent mixer (MC), and the mixed mobile phase is pumped into the component concentration column (M) with a gradient in the mixing ratio between the two mobile phases to elute the trapped target component in the sample. A homogeneous solution is formed by allowing the sample band containing the target component to diffuse by changing the solvent passageway in the diffusion promoting device (DU). Since this homogeneous solution is introduced into the separation column, theoretical plates of the separation column to be used for assessment of the target component increases and the shape of the corresponding peak is improved in the low flow velocity gradient high performance liquid chromatography system.

In summary, the system according to the present invention is featured in remarkable improvement of quantitative detection sensitivity of the target component in the separation column.

The pump as used herein is a solvent pump for the high performance liquid chromatography system, and preferably a solvent pump for the low flow velocity high performance liquid chromatography system. The valve is, for example a ten-way valve or a six-way valve for the high performance liquid chromatography system. The injector is a device for injecting the sample solution into the high performance liquid chromatography system. The separation column is a column for separating the target component in the sample, and a so-called normal phase column and reversed phase column are appropriately used depending on purposes. These devices are commercially available.

Another system for low flow velocity gradient high performance liquid chromatography according to the present invention is described with reference to FIG. 9. FIG. 9 illustrates the low flow velocity gradient high performance liquid chromatography system in which the solvent pump (P1), switching valve (V), solvent mixer (MC) and the switching valve (V) are sequentially connected in one line; the solvent pump (P2), the switching valve (V), diffusion promoting device (DU), separation column (C) and detector are separately connected; and the switching valve (V), component concentration column (M) and switching column are further connected in a different line.

The concentration and separation method of the components in the system shown in FIG. 9 is as follows.

(A) The mobile phase (1) is discharged from the solvent pump (1) to fill the solvent mixer (MC). The sample solution is injected into the component concentration column connected to the switching valve (V) through an injection port of the switching valve and, after allowing the target component in the sample to be trapped with the component concentration column, the column is washed with an appropriate solvent so that the target component is not eluted from the membrane.

(B) Then, the mobile phase for sample separation is pumped from the pump (P2) into the solvent mixer (MC), component concentration column, separation column (C) and detector (D) by turning the switching valve (V). The mobile phase 1 and the mobile phase for sample separation are mixed in the solvent mixer (MC), and the mixed solvent is pumped into the component concentration column with a gradient in the mixing ratio between the two solvents. The target component in the trapped sample is eluted, and the sample band containing the target component is allowed to diffuse in the diffusion promoting device (DU) by switching the solvent flow passageway to form a homogeneous solution. The solution flows through the separation column (C) to separate the target component. The direction of the solvent flow passageway of the mobile phase for sample separation flowing through the component concentration column is opposite to injection direction of the sample solution. The sample solution may be manually injected into the component concentration column in the system shown in FIG. 9, thereby enabling a large scale processing and high speed concentration of the sample solution.

According to the present invention, detection sensitivity of the target component can be improved by connecting the diffusion promoting device at just before the separation column in the low flow velocity gradient high performance liquid chromatographic apparatus.

EXAMPLE

Effect of configuration of the diffusion promoting device on the peak height and theoretical plate of the target component in the low velocity gradient high performance liquid chromatographic apparatus Peak shapes in the chromatogram were assessed after injecting sample components into a low velocity gradient high performance liquid chromatographic apparatus as shown in FIG. 8, wherein either a linear union as shown in FIG. 1, a linear union having a frit as shown in FIG. 2, or a three-way union having a different angles between the solvent inlet tube and outlet tube as shown in FIG. 5, 6 or 7 was connected as the diffusion promoting device (DU). Peaks obtained by using a low velocity gradient high performance liquid chromatographic apparatus in which no diffusion promoting device was connected were also assessed as references.

The sample components used were n-propyl benzoate (A), benzyl benzoate (B), n-butyl benzoate (C) and n-hexyl benzoate (D), and each sample was dissolved in an aqueous solution containing 10% of acetonitrile in a concentration of 10 µg/ml. The injection volume of the sample solution was 10 µl.

Figure 10:
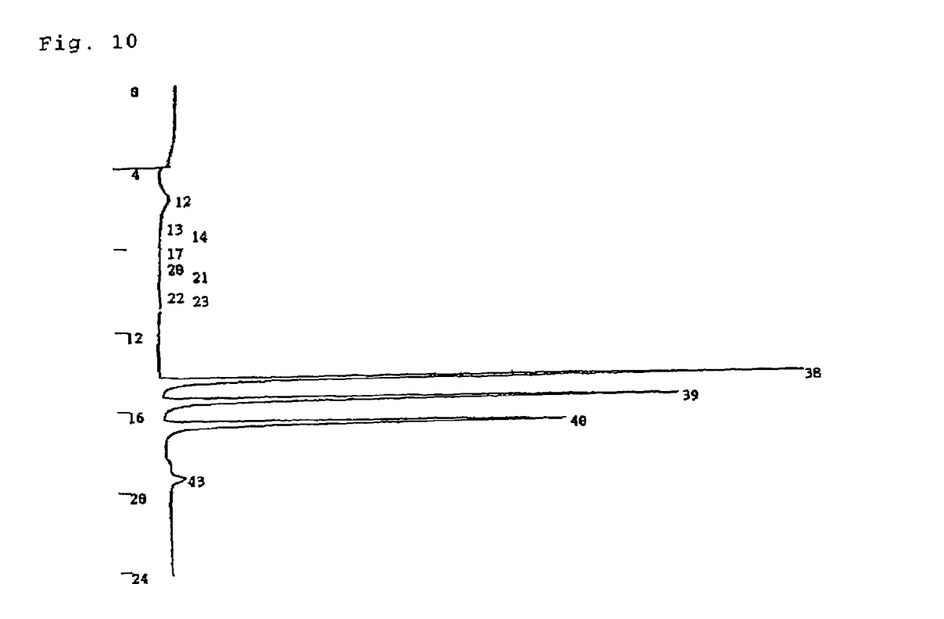
FIG. 10 shows a chromatogram obtained by using a low flow velocity gradient high performance chromatographic apparatus in which no diffusion promoting device is connected.

FIGS. 10 to 15 shows the chromatograms when the respective diffusion promoting devices having different shapes with each other are connected in the low velocity gradient liquid chromatographic apparatus. The chromatograms of the sample components A to D are shown in FIG. 10 when no diffusion promoting device is connected, in FIG. 11 when the diffusion promoting device shown in FIG. 1 is connected, in FIG. 12 when the diffusion promoting device shown in FIG. 2 is connected, in FIG. 13 when the diffusion promoting device shown in FIG. 5 is connected, in FIG. 14 when the diffusion promoting device shown in FIG. 6 is connected and in FIG. 15 when the diffusion promoting device shown in FIG. 7 is connected, respectively, to the low velocity gradient liquid chromatographic apparatus.

The peak of each sample component was sharpened in the chromatograms (FIGS. 11 to 15) obtained by using the low velocity gradient high performance liquid chromatographic apparatus in which respective diffusion promoting devices are connected, as compared with the chromatogram (FIG. 10) obtained by using the low velocity gradient high performance liquid chromatographic apparatus in which no diffusion promoting device is connected. In particular, increase of the peak heights of the sample components (B) and (C) was remarkable.

The peak heights and theoretical plates were calculated with respect to the component (C) as assessment items of the peaks in the chromatograms from the chromatograms shown in FIGS. 10 to 15, in order to investigate the effect of each configuration of the diffusion promoting device on both factors.

In general, peak resolution becomes insufficient in the assay of a mixture when the peak width of the target component is broadened and overlapped with the adjoining peaks. Accordingly, an experimental condition that prevent the peaks from being broadened should be determined, and a theoretical plate (N) is usually used as a measure of the peak broadening. The theoretical plate is expressed as $(4 VR/W)^2$, wherein VR is the retention time of the target component and W is the peak width of the target component.

The experimental results were summarized in Table 1.

TABLE 1

| Configuration of the diffusion promoting device | Peak height | Theoretical plate (N) |
|---|---|---|
| No device | 83640 | 38612 |
| Linear union (no frit) | 136915 | — |
| Linear union (with frit) | 128862 | 71728 |
| Flow passageways crossing at an acute angle | 125570 | — |
| Flow passageways crossing at a rect angle | 108062 | 66915 |
| Flow passageways crossing at an obtuse angle | 122534 | — |

The peak height of the target component and theoretical plate of the separation column were clearly improved by using the low flow velocity gradient high performance liquid chromatographic apparatus in which the diffusion promoting device was connected, as compared with those obtained by using the low flow velocity gradient high performance liquid chromatographic apparatus in which no diffusion promoting device was connected. Few differences in both factors ascribed to the difference of the configurations of the diffusion promoting device were observed.

Figure 11:
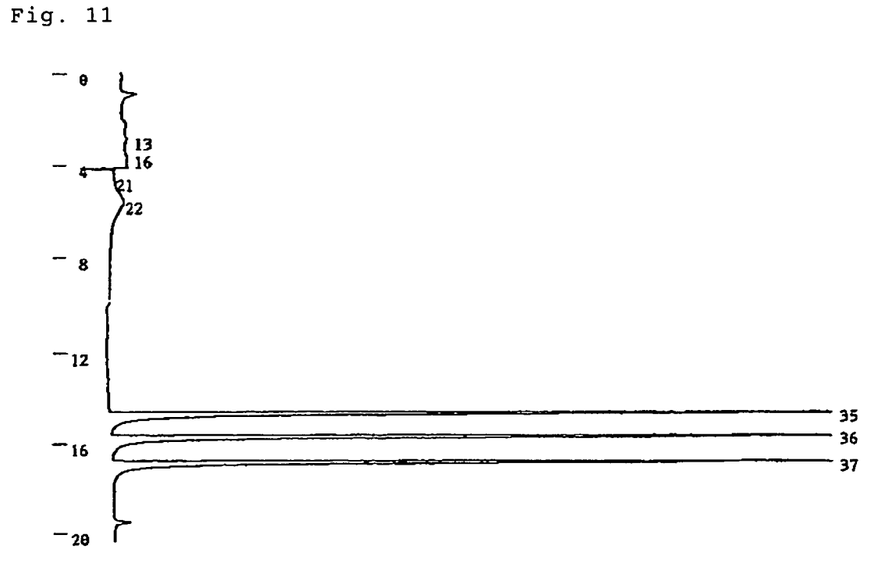
FIG. 11 shows a chromatogram obtained by using a low flow velocity gradient high performance chromatographic apparatus in which a diffusion promoting device according to the present invention shown in FIG. 1 is connected.
Figure 12:
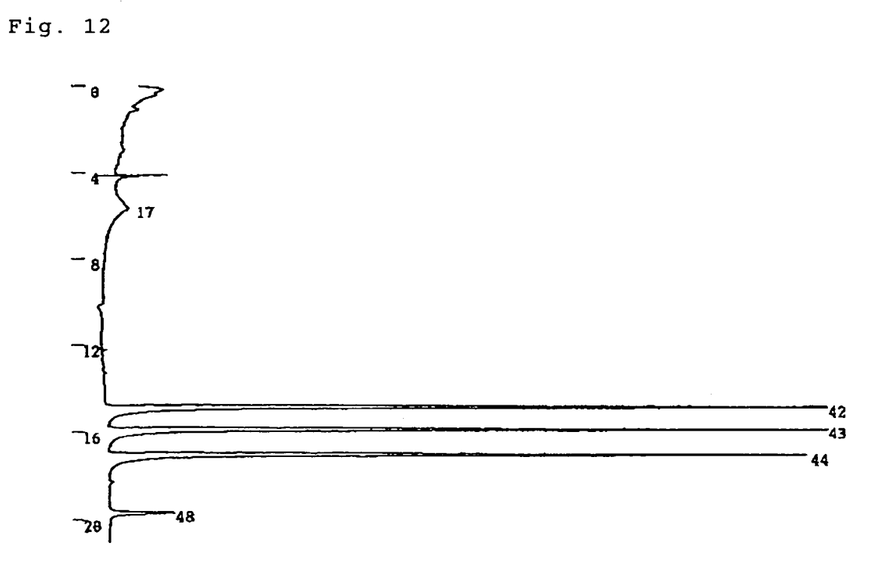
FIG. 12 shows a chromatogram obtained by using a low flow velocity gradient high performance chromatographic apparatus in which a diffusion promoting device according to the present invention shown in FIG. 2 is connected.
Figure 13:
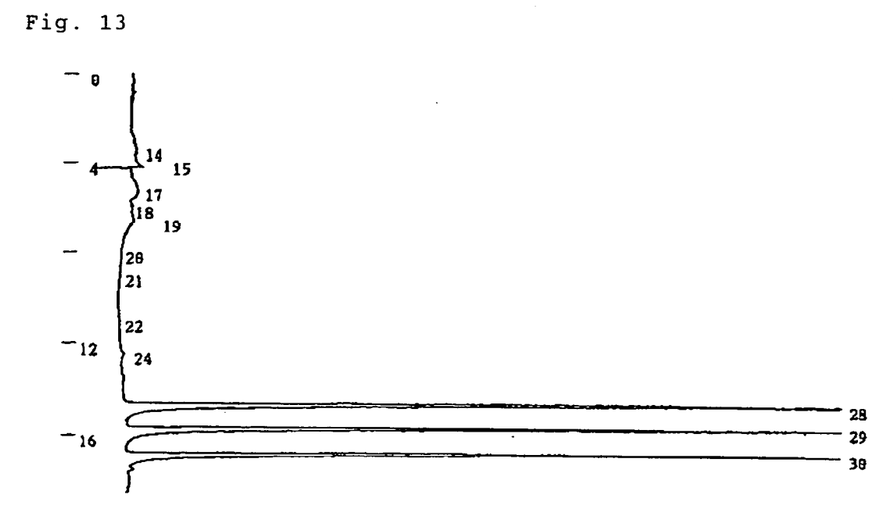
FIG. 13 shows a chromatogram obtained by using a low flow velocity gradient high performance chromatographic apparatus in which a diffusion promoting device according to the present invention shown in FIG. 5 is connected.
Figure 14:
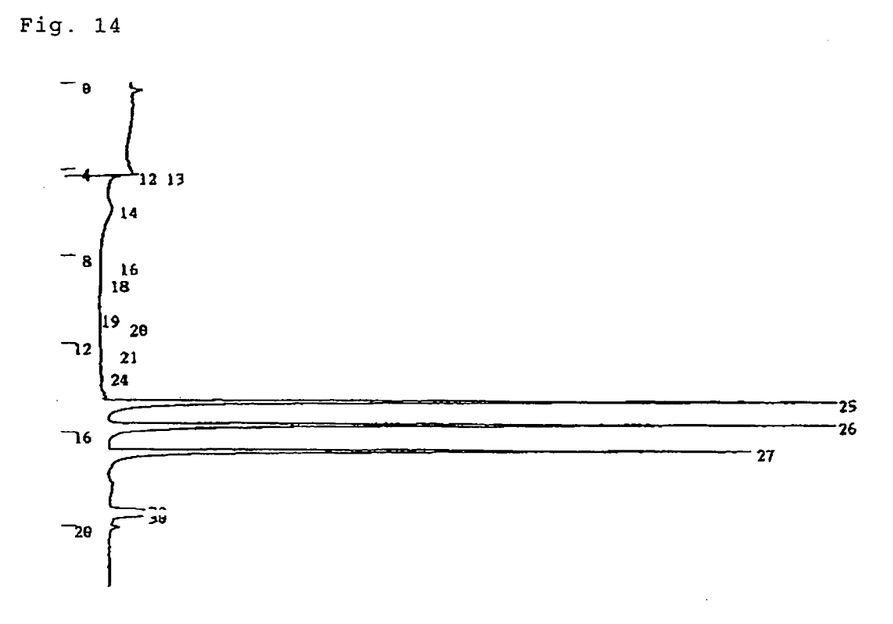
FIG. 14 shows a chromatogram obtained by using a low flow velocity gradient high performance chromatographic apparatus in which a diffusion promoting device according to the present invention shown in FIG. 6 is connected.
Figure 15:
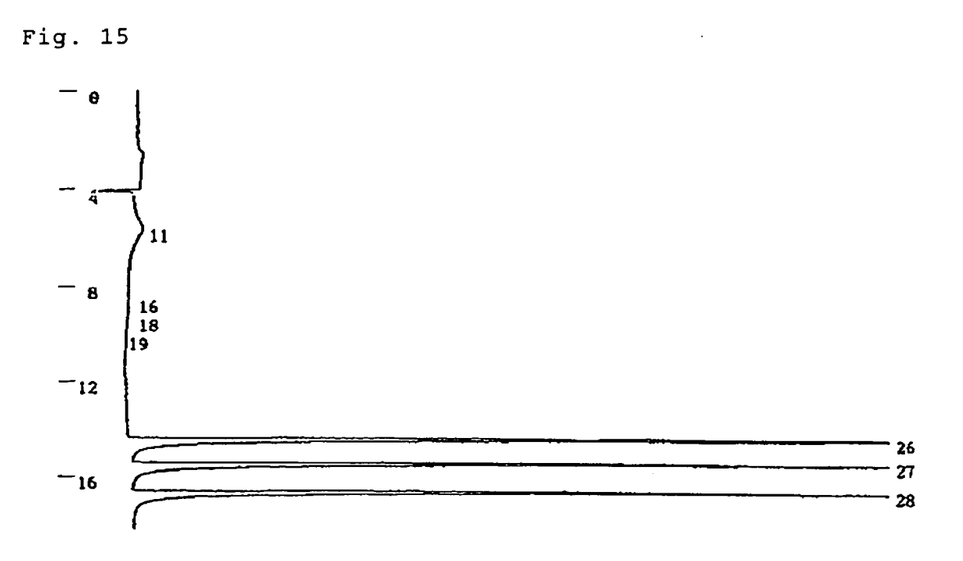
FIG. 15 shows a chromatogram obtained by using a low flow velocity gradient high performance chromatographic apparatus in which a diffusion promoting device according to the present invention shown in FIG. 7 is connected.

However, as shown in FIGS. 11, 13 and 15, calculation of the theoretical plate was impossible when the peak is so sharpened that its tip reached beyond the upper limit on the recording paper as a result of using the diffusion promoting device.

Further, clogging of neither the tube placed at just before the separation column nor the separation column itself was observed in the low flow velocity high performance gradient liquid chromatographic apparatus in which the diffusion promoting device was connected.

As hitherto described in detail, the diffusion promoting device according to the present invention that is connected at just before the separation column clearly has a function for improving detection sensitivity in the low flow velocity high performance gradient liquid chromatographic apparatus.

The experimental data in Table 1 and chromatograms in FIGS. 10 to 15 were obtained by the following experimental conditions.

Detector: UV absorption photometer (measuring wavelength: 254 nm)

Separation column: Inertsil ODS-2 (0.7 mm I.D×150 mm)

Mobile phase for concentration: aqueous solution containing 0.1% ammonium acetate Mobile phase for sample separation: mixed solution of acetonitrile containing 0.1% ammonium acetate and ethanol (500:500)

Flow Velocity

Mobile phase for for sample concentration: 1.0 ml/min

Mobile phase for sample separation: 0.025 ml/min

What is claimed is:

1. A high performance liquid chromatographic apparatus size-dimensioned to have a flow velocity gradient of 250 microliters per minute or less, said apparatus in which a solvent pump (P1), an injector (I), and a switching valve (V) are connected in this order in one line; and a solvent pump (P2), a switching valve (V), a diffusion promoting device (DU) that comprises a solvent inlet tube and a solvent outlet tube, wherein said device includes at least one feature selected from the group consisting of (ii) having a solvent outlet tube connected to a solvent inlet tube at an acute angle, a right angle, or an obtuse angle and (iii) having a solvent outlet tube connected to a solvent inlet tube by a connecting part having a diameter that is larger than the diameters of the diameters of the solvent inlet and outlet tubes, a separation column (C), and a detector (D) are connected in another line.

2. A high performance liquid chromatographic apparatus apparatus size-dimentioned to have a flow velocity gradient of 250 microliters per minute or less, said apparatus in which a solvent pump (P1), a switching valve (V), a solvent mixer (MC), and a switching valve (V) are connected in this order in one line; a solvent pump (P2), a switching valve (V), a diffusion promoting device (DU) that comprises a solvent inlet tube and a solvent outlet tube, wherein said device includes at least one feature selected from the group consisting of (i) having a solvent inlet tube and a solvent outlet tube with different inner diameters, (ii) having a solvent outlet tube connected to a solvent inlet tube at an acute angle, a right angle, or an obtuse angle, and (iii) having a solvent outlet tube connected to a solvent inlet tube by a connecting part having a diameter that is larger than the diameters of the diameters of the solvent inlet and outlet tubes, a separation column (C), and a detector (D) are connected in another line; and a switching valve (V), a component concentration column (M), and a switching valve (V) are connected in a different line.

3. The high performance liquid chromatographic apparatus of claim 2, wherein the diffusion promoting device (i) has a solvent inlet tube and a solvent outlet tube with different inner diameters.

4. The high performance liquid chromatographic apparatus of claim 2, wherein the diffusion promoting device (ii) has a solvent outlet tube connected to a solvent inlet tube at an acute angle, a right angle, or an obtuse angle.

5. The high performance liquid chromatographic apparatus of claim 4, wherein the diffusion promoting device (ii) has a solvent outlet tube connected to a solvent inlet tube at a right angle.

6. The high performance liquid chromatographic apparatus of claim 2, wherein the diffusion promoting device (iii) has a solvent outlet tube connected to a solvent inlet tube by a connecting part having a diameter that is larger than the diameters of the diameters of the solvent inlet and outlet tubes.

* * * * *